United States Patent
Devlin, Sr. et al.

(10) Patent No.: US 7,101,715 B2
(45) Date of Patent: Sep. 5, 2006

(54) INCREASING THROUGHPUT OF AN AUTOMATIC CLINICAL ANALYZER SYSTEM BY PARTITIONING ASSAYS ACCORDING TO FREQUENCY OF REQUESTED PERFORMANCE

(75) Inventors: William Jackson Devlin, Sr., Lincoln University, PA (US); David R. Thompson, Kennett Square, PA (US)

(73) Assignee: Dade Behring Inc., Deerfield, IL (US)

( * ) Notice: Subject to any disclaimer, the term of this patent is extended or adjusted under 35 U.S.C. 154(b) by 73 days.

(21) Appl. No.: 10/245,245

(22) Filed: Sep. 17, 2002

(65) Prior Publication Data

US 2004/0053414 A1    Mar. 18, 2004

(51) Int. Cl.
   *G01N 35/02*    (2006.01)
   *G01N 33/50*    (2006.01)
(52) U.S. Cl. .............................. 436/43; 436/50; 422/63; 422/68.1; 422/64; 422/65
(58) Field of Classification Search ................. 422/63, 422/64, 65, 68.1; 436/43, 50
   See application file for complete search history.

(56) References Cited

U.S. PATENT DOCUMENTS

| | | | | |
|---|---|---|---|---|
| 4,678,752 A | * | 7/1987 | Thorne et al. ............ | 435/287.3 |
| 4,965,049 A | * | 10/1990 | Lillig et al. ................ | 422/68.1 |
| 5,087,423 A | * | 2/1992 | Ishibashi ..................... | 422/67 |
| 5,282,149 A | * | 1/1994 | Grandone et al. ............ | 702/19 |
| 5,482,861 A | * | 1/1996 | Clark et al. .................. | 436/48 |
| 5,575,976 A | | 11/1996 | Choperena et al. .......... | 422/64 |
| 5,972,295 A | | 10/1999 | Hanawa et al. ............... | 422/65 |
| 6,019,945 A | | 2/2000 | Ohishi et al. ................ | 422/65 |
| 6,022,746 A | | 2/2000 | Fritchie et al. .............. | 436/50 |
| 6,117,392 A | | 9/2000 | Hanawa et al. .............. | 422/65 |
| 6,117,683 A | | 9/2000 | Kodama et al. ............. | 436/47 |
| 6,141,602 A | | 10/2000 | Igarashi et al. ............. | 700/226 |

* cited by examiner

*Primary Examiner*—Jill Warden
*Assistant Examiner*—LaToya I Cross
(74) *Attorney, Agent, or Firm*—Leland K. Jordan (57) ABSTRACT

A dual analyzer system comprising at least two analyzers where samples to be tested are partitioned into three groups in accord with the frequency the test assays are requested. One analyzer performs a portion of the most frequently menu assays and all of a first subgroup of less frequently requested assays. The second analyzer performs a similar portion of the most frequently menu assays and all of a second subgroup of less frequently requested assays. The first of the analyzers is not equipped to perform any of the second subgroup of assays and the second analyzer is not be equipped to perform any of the second subgroup of assays.

4 Claims, 7 Drawing Sheets

INCREASING THROUGHPUT OF AN AUTOMATIC CLINICAL ANALYZER SYSTEM BY PARTITIONING ASSAYS ACCORDING TO FREQUENCY OF REQUESTED PERFORMANCE

FIELD OF THE INVENTION

The present invention relates to a method and apparatus for automatically processing a patient's biological fluids such as urine, blood serum, plasma, cerebrospinal fluid and the like. In particular, the present invention provides an improved method to process patient samples in a analyzing system having at least two analyzers each adapted to perform a number of different clinical assays using different assay technologies.

BACKGROUND OF THE INVENTION

Various types of tests related to patient diagnosis and therapy can be performed by analysis assays of a sample of a patient's infections, bodily fluids or abscesses. Such patient samples are typically placed in sample vials, extracted from the vials, combined with various reagents in special reaction vessels or tubes, incubated, and analyzed to aid in treatment of the patient. In typical clinical chemical analyses, one or two assay reagents are added at separate times to a liquid sample having a known concentration, the sample-reagent combination is mixed and incubated. Interrogating measurements, turbidimetric or fluorometric or absorption readings or the like are made to ascertain endpoint or rate values from which an amount of analyte may be determined using well-known calibration techniques.

Although various known clinical analyzers for chemical, immunochemical and biological testing of samples are available, analytical clinical technology is challenged by increasing needs for improved levels of analysis. Due to increasing demands on clinical laboratories regarding assay throughput, there continues to be a need for improvements in the overall performance of automated clinical analyzers. In particular, sample analysis continuously needs to be more cost effective in terms of reduced testing turnaround time which has previously addressed by increasing analyzer throughput, and, more recently, by linking together a number of analyzers and shuttling samples between the analyzers.

An important contributor to maintaining a high throughput of automatic analyzers is the ability to quickly process a plurality of samples through a variety of different assay process and signal measurement steps. One method to achieve this feature is to link together analyzers of different types, each adapted to perform a certain catalog of assays. Another is to link together two or more analyzers of the same type and to allocate incoming samples to whichever analyzer has the smallest backlog of samples to process. Alternately, incoming samples may be allocated between analyzers according to the number and availability of assay resources (reaction vessels, reagents, etc) required by the assay and duplicated on each analyzer. What has been overlooked, however, in such multi-analyzer systems, is that the frequencies at which various assays are requested of analyzer may be greatly different from one another and how this might play a key role in increasing throughput and/or reliability of multi-analyzer systems.

U.S. Pat. No. 6,261,521 discloses a sample analysis system having a plurality of analysis units placed along a main conveyor line prior to its analysis operation. The system setup includes setup of analysis units in combination with different types of reagent supply units, setup of analysis routes as to whether it is a stationary type or an automatic type, and setup of analysis items for each analysis unit as to which analysis item should be assigned to which analysis unit having which reagent supply type.

U.S. Pat. No. 6,117,392 discloses an automatic analyzing apparatus having a rack supply unit capable of containing sample racks, an analyzing unit for testing a sample sampled from a sample container contained in the sample rack, a transfer line for transferring a sample rack supplied from the rack supply unit to a position corresponding to the analyzing unit and transferring the sample rack after being sampled to an exit of the transfer line, a standby unit for keeping sample racks having a probability of being reexamined standing-by, a returning line for returning the sample rack after being sampled to an entrance side of the transfer line, and a rack collecting unit for containing sample racks not required to be reexamined.

U.S. Pat. No. 6,022,746 discloses a method for operating a multi-analyzer system by generating a list of tests to be performed by the system within a given reaction vessel. The list of tests is sorted according to the number of reaction vessels used in performing each test to be performed by the system in a given time period. A duplication percentage for the tests is determined and is compared with the sorted list of tests. Resources associated with the tests are duplicated across at least two analyzers based on the comparison of the duplication percentage with the sorted list of tests in a matter that at least one of the tests is performed by at least two of the analyzers.

U.S. Pat. No. 6,019,945 discloses a transfer mechanism for transferring a sample container holder between a conveyor line and a sampling area formed in each of several analyzers, the transfer mechanism being connectable to each one of the plurality of analyzers. At least two analyzers units are different from one other in either the types of reagent supply means, the number of analysis items that can be analyzed, the number of tests that can be processed in a unit time, or the species of samples to be processed, and wherein the at least two analysis units described above have the same attachment mechanism or the same shape thereof with respect to the conveyor line.

U.S. Pat. No. 5,972,295 discloses an automatic analyzers comprising a rack supply unit capable of containing sample racks, an analyzing unit for testing an instructed analysis item to a sample sampled from a sample container contained in the sample rack, a transfer line for transferring a sample rack supplied from the rack supply unit to a position corresponding to the analyzing unit and transferring the sample rack after being sampled to an exit of the transfer line, a standby unit for keeping sample racks having a probability of being reexamined stand-by, a returning line for returning the sample rack after being sampled to an entrance side of the transfer line, and a rack collecting unit for containing sample racks not required to be reexamined.

U.S. Pat. No. 5,966,309 discloses an automated apparatus for subjecting samples to one or more selected test procedures at one or more test stations comprising a conveyor line for transporting samples contained in uniquely labeled containers, said line having at least two lanes for routing said containers to one or more selectable test stations, at least one of said lanes being a transport lane and at least one of said lanes being a queue line, and having a container interface device for transferring containers to said testing device from the queue lane and back again onto said queue lane.

U.S. Pat. No. 5,902,549 discloses a plurality of analyzer units for serum, a plurality of analyzer units for blood plasma, and a plurality of analyzer units for urine are arranged along a main transfer line for transferring a sample rack from a rack providing portion to a rack storage portion. A reagent bottle for inspecting liver function is contained in each reagent delivery mechanism of two analyzer units among the plurality of analyzer units for serum. When the reagent for inspecting liver function in one of the two analyzer units is to be short, analysis for the liver function analysis item in the samples can be continued by transferring a sample rack from the rack providing portion to the other analyzer unit.

U.S. Pat. No. 5,380,488 discloses a container feeding system which includes a feed stocker for stocking racks holding containers, one or more sampling feeders connected to the downstream side of the feed stocker, and one or more analyzers for withdrawing samples from containers which are moved to sampling positions in an interlocked relation to the sampling feeder or feeders. One or more coupling feeders are connected to the respective downstream sides of the sampling feeder or feeders, and a treated container stocker is connected to the most downstream side of the coupling feeder or feeders. The individual components are provided as respective units. The number of sampling feeders and coupling feeders connected thereto can be increased or reduced, and in correspondence therewith so can the number of analyzers disposed along a rack feeding line. The rack feeding path can thus be readily increased and reduced, as desired, to meet the scale of the delivery side. Likewise, the control mechanism for controlling the feeding of containers with selective priority is also greatly simplified.

U.S. Pat. No. 5,087,423 discloses a plurality of analyzing modules, a plurality of analyzing routes and at least one bypass route bypassing at least one analyzing module are arranged. Each analyzing module is capable of analyzing samples with respect to one or more items, and samples successively supplied from the introduction sides of the modules are selectively delivered into each module in accordance with the possible analyzing items of each module and the analyzing items of the samples to be analyzed. The sample cup can pass the module via a bypass or can be returned to the introduction side of the module via a bypass, in accordance with the items to be analyzed, the effective distribution of the sample cups can be performed.

From this discussion of the art state in automated clinical analyzers, it may be seen that while has been considerable progress has been made toward increasing processing efficiency, there remains an unmet need for a system and apparatus that provides a high volume throughput for different type assays, in particular for those combinations of different type assays when a smaller percentage of different assay types are requested to be performed a larger percentage of the total assays requested, and when conversely, when a larger percentage of different assays are requested to be performed a smaller percentage of the total assays requested. In addition, little progress has been made toward increasing the reliability of operation of a dual analyzer system comprising at least two analyzers by providing back-up operational capability for instances covering the larger percentage of the total assays requested.

SUMMARY OF THE INVENTION

The principal object of the invention is to provide a method for using an automatic clinical dual analyzer system comprising at least two analyzers in a manner that achieves high throughput irregardless of the mix of different assays required to be performed by the analyzer for different samples presented to the dual analyzer system, without unduly sacrificing overall system reliability. Each analyzer includes a circular rotatable assay reaction carousel for holding reaction vessels and providing stepwise movements in a constant circular direction at a constant velocity, the stepwise movements being separated by constant stationary dwell times, during which dwell time an assay device may operate on an assay mixture contained within a reaction vessel. A dual analyzer system like those on which the present invention may be performed typically has a plurality of conventional assay operation stations at which are positioned individual assay devices, such as sensors, reagent add stations, mixing stations, separation stations, and the like.

In a first embodiment of the present invention, a larger percentage of the most frequently menu assays requested to be performed are assigned into a first subgroup comprising a smaller number of the total number of different menu assays and both analyzers in a dual analyzer system are equipped to perform this totality of assays. The remaining assays to be performed are divided into two smaller separate and distinct subgroups, so that the totality of assays in the three groups comprise the full list of requested assays. The two smaller groups comprise a smaller percentage of the most frequently menu assays requested to be performed. Importantly, the total number of different assays in the two smaller groups comprise a larger number of the total number of different menu assays, even though their frequency of being requested is a smaller number of the total number of requested menu assays. A key feature of the present invention is that a first of the two analyzers would be equipped with necessary reagents or other specialty items as required to perform all of those assays of the first subgroup and of a first of the two smaller separate and distinct subgroups, and would not be equipped to perform any of those assays of the second of the two smaller subgroups. Similarly, the second analyzer in the system would be equipped with necessary reagents or other specialty items as required to perform all of those assays of the first subgroup and of a second of the two smaller separate and distinct subgroups, and would not be equipped to perform any of those assays of the first of the two smaller subgroups.

In an alternate embodiment of the invention, the first of the two analyzers would be equipped with necessary reagents or other specialty items as required to perform all of those assays of the first subgroup and would not be equipped to perform any of those assays of either of the two smaller subgroups. In this embodiment, the second analyzer in the system would be equipped with necessary reagents or other specialty items as required to perform all of those assays of the first subgroup and of both of the two smaller separate and distinct subgroups. Such an embodiment has the back-up reliability features of the first embodiment, however throughput of the most frequently requested assays of the first subgroup is increased.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
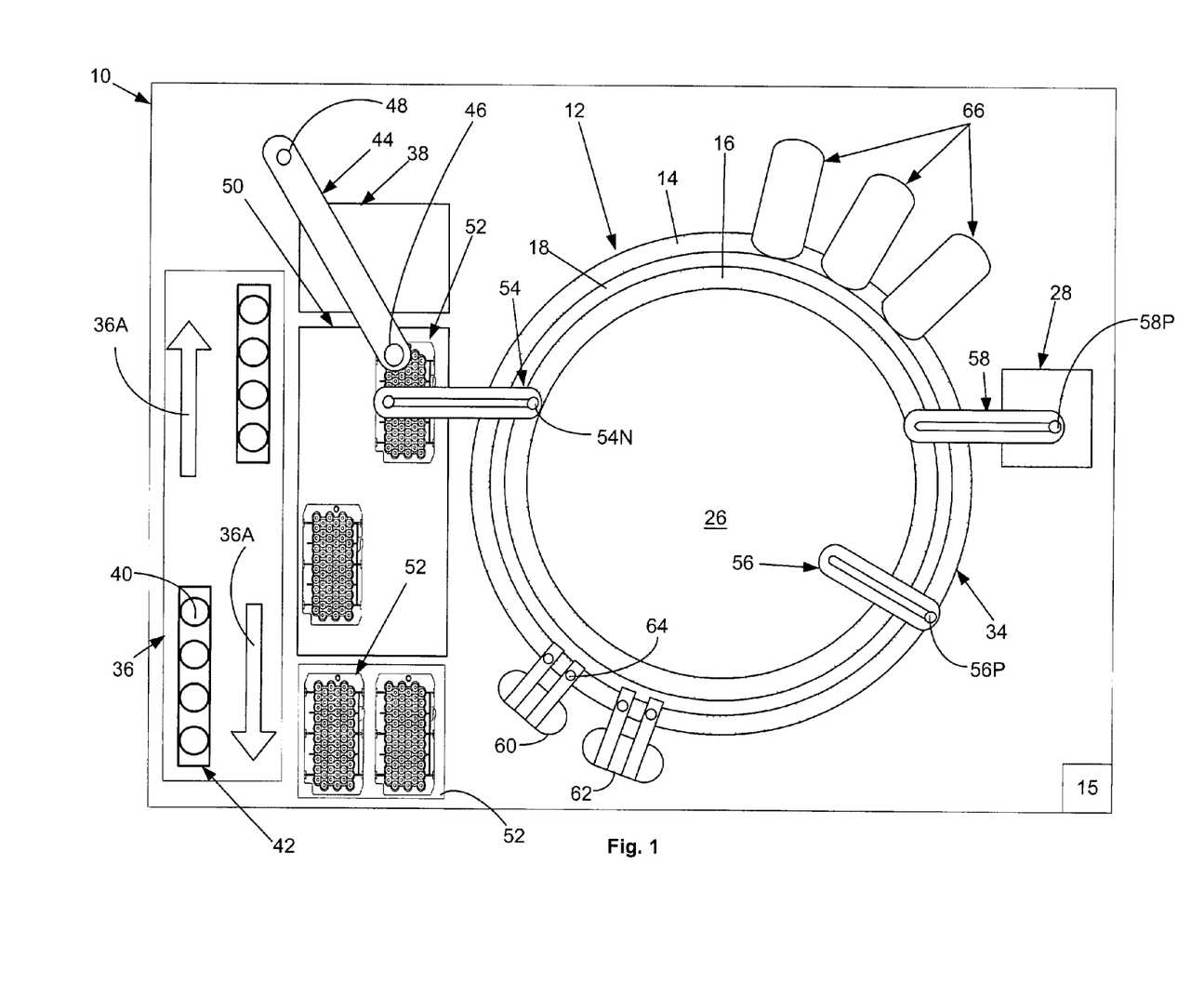
FIG. 1 is a schematic plan view of a single conventional automated clinical analyzer like those known in the art.
Figure 2:
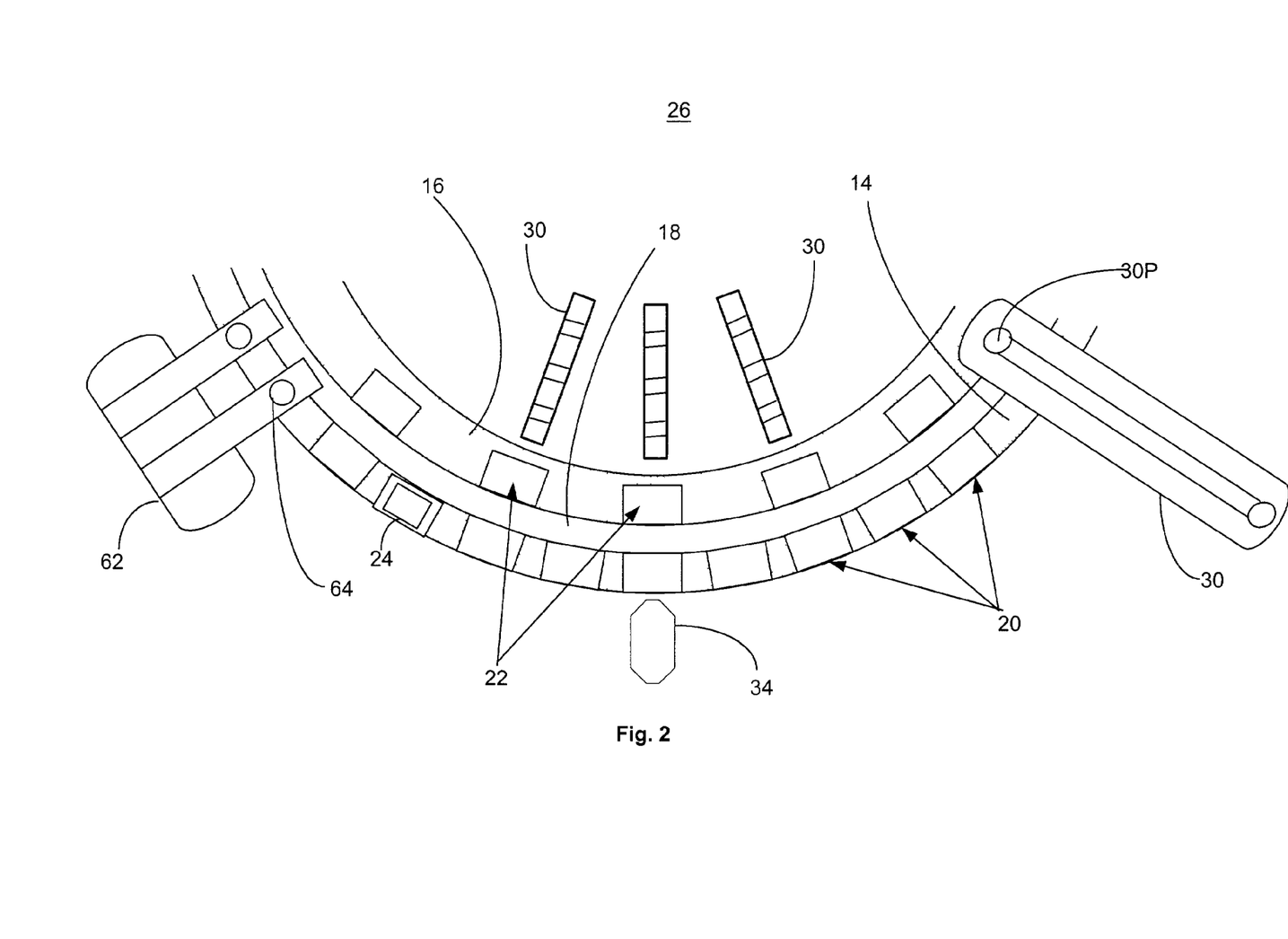
FIG. 2 is an enlarged partial schematic plan view of the automated analyzer of FIG. 1.

FIG. 1, taken with FIG. 2, shows schematically the elements of a single convention automatic chemical analyzer 10 convenient for practicing the present invention and comprising a reaction carousel 12 supporting a outer cuvette circle 14 of cuvette ports 20 and an inner cuvette circle 16 of cuvette ports 22, the outer cuvette circle 14 and inner cuvette circle 16 being separated by a open groove 18. Cuvette ports 20 and 22 are adapted to receive a plurality of reaction cuvettes 24 typically formed as small, flat walled, U-shaped containers with an open central reaction portion closed at the bottom and with an opening at the top of the cuvettes 24 to allow the addition of reagent and sample liquids. Reaction carousel 12 is rotatable using stepwise movements in a constant direction at a constant velocity, the stepwise movements being separated by a constant dwell time during which dwell time, carousel 12 is maintained stationary and an assay device located proximate carousel 12 may operate on an assay mixture contained within a cuvette 24.

Two temperature-controlled reagent storage areas 26 and 28 each store a plurality of reagent cartridges 30, cartridges 30, for example being a multi-compartmented reagent container like those described in U.S. Pat. No. 4,720,374, or co-pending application Ser. No. 09/949,132 assigned to the assignee of the present invention, and sold under the tradename FLEX(tm) cartridge by Dade Behring Inc, Deerfield, Ill., and containing reagents as necessary to perform a given assay. A selectively-opened lid (not shown) covers each of reagent storage areas 26 and 28 to allow access to cartridges 30; for simplicity, only three reagent cartridges 30 are schematically illustrated in FIG. 2 as disposed beneath a cut out portion of reagent storage area 26 however similar reagent cartridges 30 are disposed within reagent storage area 28. Shuttle means (not shown) move individual cartridges 30 to access ports for reagent probes 56P and 58P discussed later. Storage area 28 may be conveniently located external to the circumference of outer cuvette circle 14 and reagent storage area 26 may be conveniently located internal to the circumference of inner cuvette circle 16.

A clinical analyzer 10 like those on which the present invention may be performed has a plurality of conventional assay operation devices 34 disposed proximate carousel 12 and at which are positioned individual computer controlled electromechanical devices, such as sensors, reagent add stations, mixing stations, and the like, as required to perform the myriad of actions required in well known clinical assays. Such devices and their operation are well known in the art and need not be described herein. See, for example, U.S. Pat. Nos. 5,876,668, 5,575,976 and 5,482,861 and the references cited therein.

An indexing drive for the reaction carousel moves the reaction vessels in the constant direction a predetermined numbers of incremental steps. The length of the circumference of cuvette circles 14 and 16, the separation distance between cuvette ports 20 and 22, the number of cuvette ports 20 and 22, and the number of increments per indexing are selected so that any given cuvette ports 20 and 22 returns to its original starting position after a fixed number of incremental steps. Thus, all cuvette ports 20 and 22 on the reaction carousel 12 return to their original location in a full operational cycle time which is determined by the fixed number of incremental steps multiplied by the sum of dwell time at each assay device and the time required for a stepwise movement.

Figure 3A:
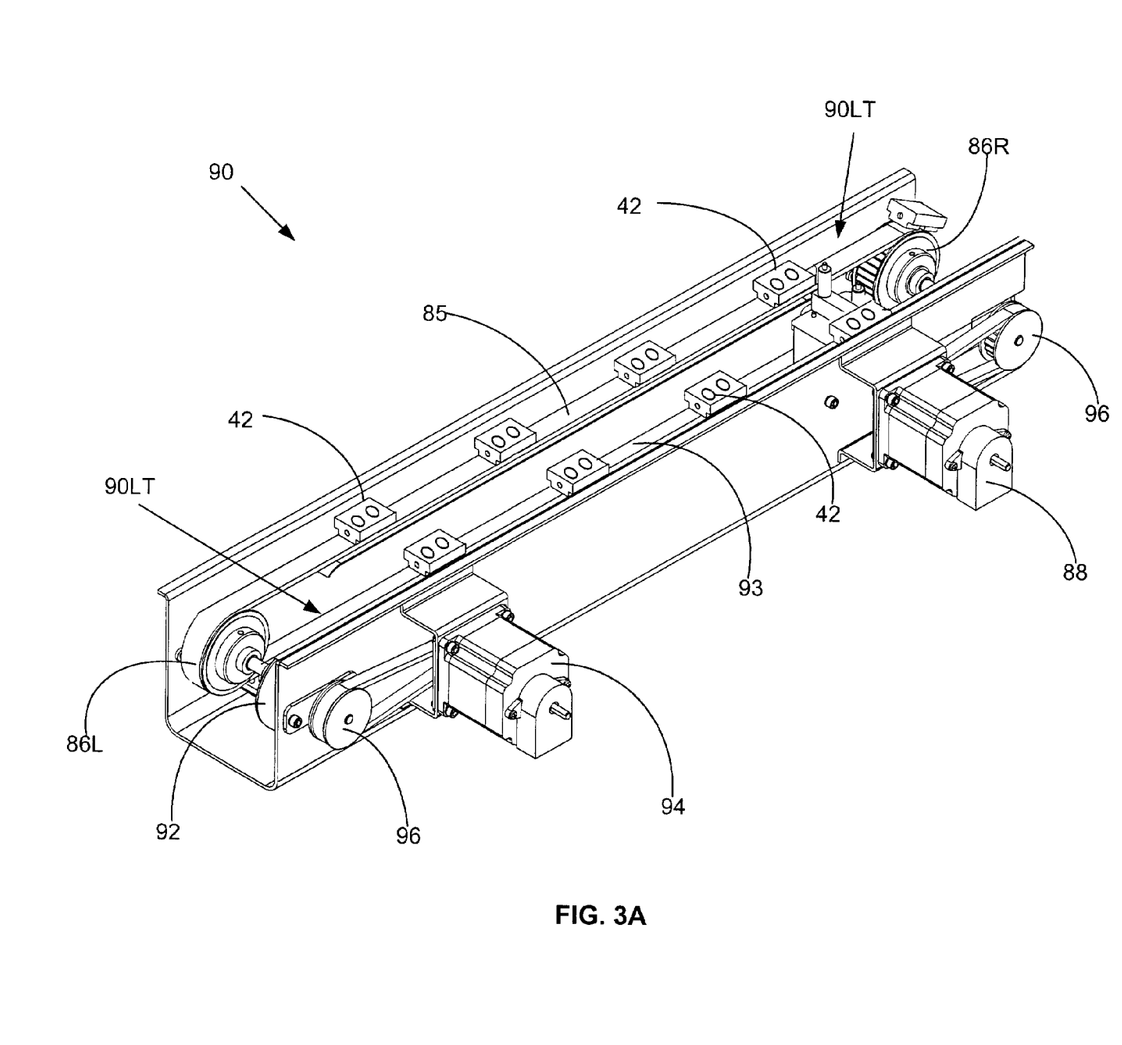
FIGS. 3A and 3B are perspective view of a sample rack transport system useful in practicing the present.

Incoming sample specimens to be tested are contained in sample tubes 40 mounted in sample tube racks 42 and transported into the arc of sampling arm 44, for example, by a bi-directional incoming and outgoing sample tube transport system 36, as indicated by open arrows 36A, and as described in co-pending application Ser. No. 09/992,917 assigned to the assignee of the present invention. This system is described here but this method of transporting sample tube racks 42 of a magnetic type is not definitive nor limiting as several other transport mechanisms are well known in the art. A magnetic drive system 90 useful in analyzer 10 for carrying out the present invention is seen in the perspective drawings of FIG. 3A to comprise at least one bi-directional linear drive transport mechanism 90LT depicted, for example, as a first belt 85 endlessly circulating around a first pair of pulleys 86, one of the first pulleys 86 being coupled to a first bi-directional motor 88, the first belt 85 and first pulleys 86 being mounted beneath and in close proximity to the operating surface of analyzer 10 which defines input and output lanes. FIG. 3A illustrates two such bi-directional linear drive transport mechanisms 90LT, however, in a first embodiment of the present invention described later in which a single incoming sample tube transport system 70 is employed, only a single bi-directional linear drive transport mechanism 90LT is required to practice the present invention. It should be understood that any of several mechanisms are capable of providing the bi-directional linear drive transport mechanism 90LT used within the present invention, for instance a bi-directional motor coupled to a linear drive screw, or a pneumatic operated plunger, both supporting the magnetic housings and having a magnet therein.

Figure 3B:
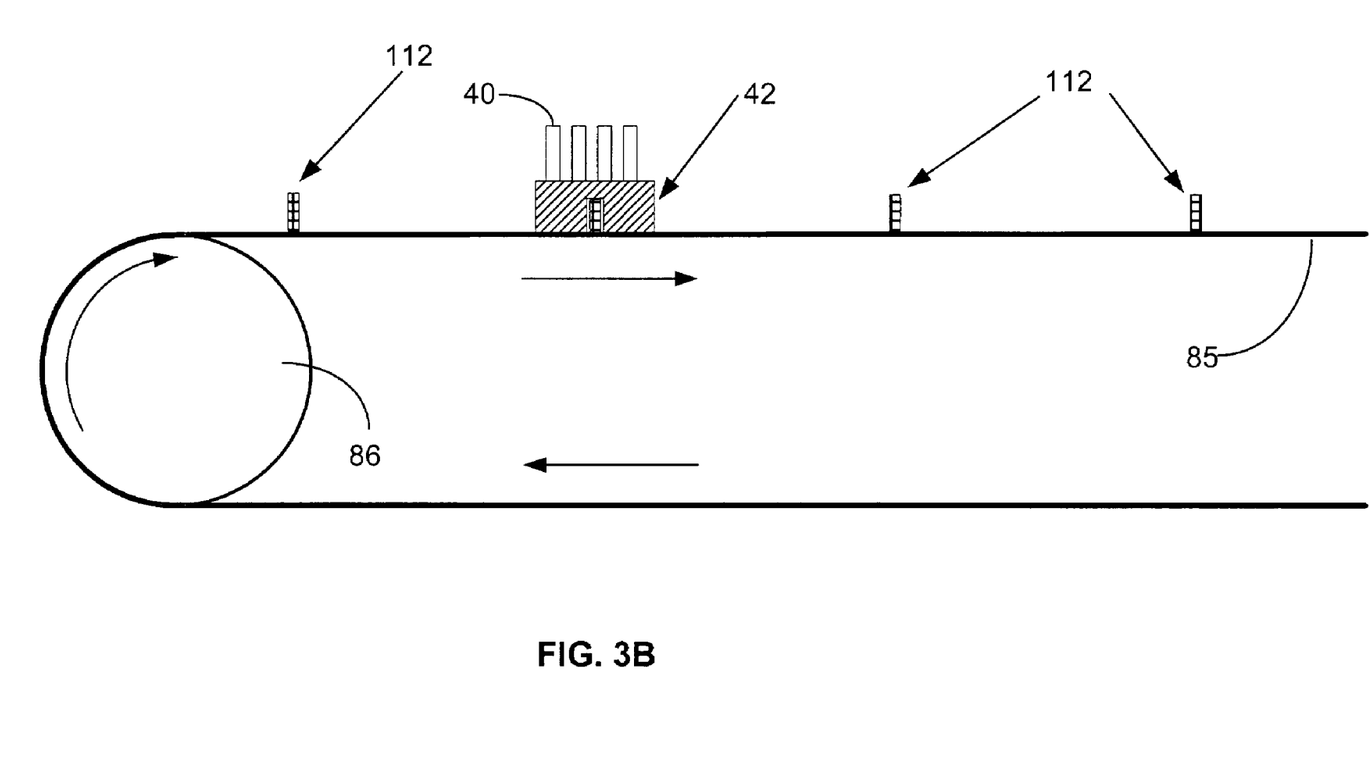

First belt 85 is driven by motor 88 in an incoming direction, for example along the direction of arrow 36A, and is located beneath the operating surface of analyzer 10. In a similar manner, magnetic drive system 90 comprises a second belt 93 endlessly circulating around a second pair of pulleys 92, one of the second pulleys 92 (only one such pulley 92 is visible) being coupled to a second bi-directional motor 94, the second belt 93 and second pulleys 92 being mounted beneath and in close proximity to the output lane 74 portion of the operating surface of analyzer 10. Second belt 93 is driven by second motor 94 in a second direction opposite to the first direction. Motors 88 and 94 are typically stepper motors independently controlled by computer 15 and have drive gears 96 coupled to pulleys 86 and 92 which are preferably formed as pulley gears interlaced with gear teeth formed on belts 85 and 93. The magnetic drive system 90 is described here in terms of a pulley-and-belt drive mechanism, however, any of a number of bi-directional linear drive mechanisms may be employed to achieve the purpose of linearly moving a sample tube rack 42 in either of two opposing directions. FIG. 3B illustrates a plurality of sample tube racks 42 coupled to each drive belt 85 and 93 by means of a plurality of upright posts 112 generally equally spaced apart by a predetermined distance, and, as seen in FIG. 3B, the plurality of upright posts 112 are attached to belts 85 and 93 at that same predetermined distance. Posts 112 are adapted by any of various mechanical techniques, such as screws, snaps, welds, etc., to secure the plurality of magnetic sample tube racks 42 to belt 85 and 93.

After sample has been aspirated by sampling arm 44 described next and deposited within aliquot wells 52W, sample tube racks 42 may optionally be inventoried within analyzer 10 inside an environmental chamber 38 as described in co-pending application Ser. No. 09/827,045 also assigned to the assignee of the present invention. Patient liquid specimens contained in open sample tubes 40 are identified by reading bar coded indicia placed thereon using a conventional bar code reader to determine, among other items, a patient's identity, the tests to be performed, if a sample aliquot is desired to be retained inside environmental chamber 38 and if so, for what period of time. It is also common practice to place bar coded indicia on sample tube racks 42 and employ a large number of conventional bar code readers installed throughout analyzer 10 in order to ascertain, control and track the location of both sample tubes 40 and sample tube racks 42. Such reader devices and the techniques for tracking are well known in the art and are not seen in FIG. 1 nor need be discussed further.

Figure 4:
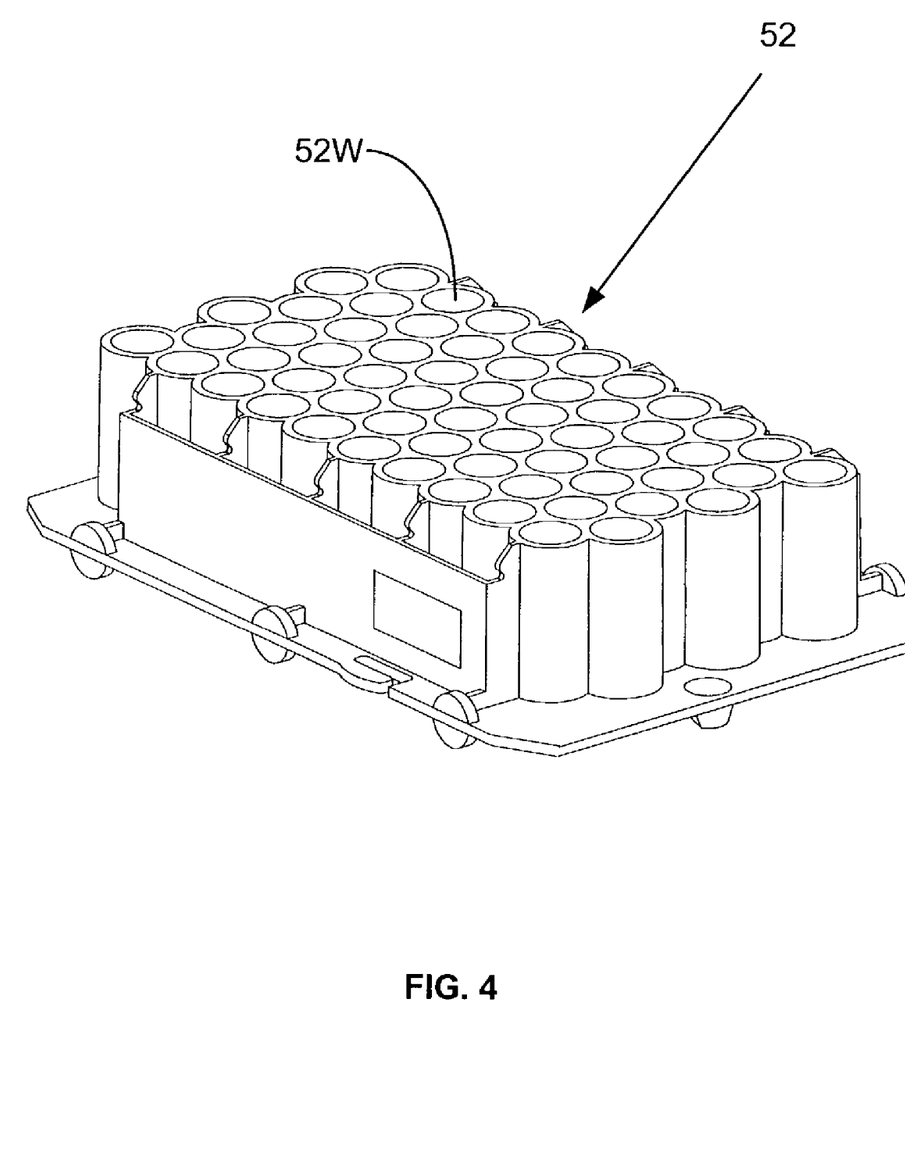
FIG. 4 is a perspective view of a multi-well aliquot vessel useful in practicing the present.

A fluid sampling arm 44 supports a conventional liquid sampling probe 46 and is mounted to a rotatable shaft 48 so that movement of sampling arm 44 describes an arc intersecting the sample tube transport system 36 and an aliquot strip transport system 50 adapted to transport multi-well aliquot vessels 52, like that seen in FIG. 4, to a conventional sample/reagent aspiration and dispense arm 54 located proximate reaction carousel 12. Sampling arm 44 is operable to aspirate liquid sample from sample tubes 40 and to dispense a sample aliquot into one or more of a plurality of aliquot wells 52W in aliquot vessels 52, depending on the quantity of sample required to perform the requisite assays and to provide for a sample aliquot to be retained by analyzer 10 within environmental chamber 38. Another sample aspiration and dispense arm 54 is controlled by computer 15 and is adapted to aspirate a controlled amount of sample from wells 52W via a conventional nozzle 54N and to dispense an appropriate amount of aspirated sample into one or more cuvettes 24 for assay testing for one or more analytes. After sample has been dispensed into reaction cuvettes 24 in cuvette ports 20 and 22, conventional transfer means move aliquot strips 52 as required between aliquot strip transport system 50 and environmental chamber 38 or, optionally, to a waste disposal area, not shown.

Analyzer 10 is controlled by computer 15 based on software written in a machine language, like that used on the Dimension® clinical chemistry analyzer sold by Dade Behring Inc, of Deerfield, Ill., and widely used by those skilled in the art of computer-based electromechanical control programming. At least two reagent aspiration and dispense arms 56 and 58 comprising a pair of conventional liquid reagent probes, 56P and 58P, respectively, are independently mounted and translatable between reagent storage areas 36 and 28, respectively. Probes 56P and 58P are shown in FIG. 1 in two operating positions, with one probe, 56P, adapted to remove reagent from a reagent container in storage area 26 and to dispense aspirated reagent into cuvettes 22 and 24 located in cuvette circles 14 and 16 and with the other probe, 58P, adapted to remove reagent from a reagent container in storage area 28 and to dispense aspirated reagent into cuvettes 22 and 24 located in cuvette circles 14 and 16. Probes 56P and 58P typically comprise an ultrasonic mechanism used for hydrating, aspirating, dispensing and mixing reagents. The hydrating, aspirating, dispensing and mixing mechanisms have features well known in the art and need not be described further.

Cuvette load and unload stations 60 and 62 are positioned proximate outer cuvette carousel 14 and are conventionally adapted to load cuvettes 24 into cuvette ports 20 and 22 seen in FIG. 2 formed in outer cuvette carousel 14 and inner carousel 16 using for example a translatable robotic clamp 64. Conventional sample processing devices 34 (FIG. 2), are positioned at selected circumferential locations about the reaction carousel 12 in order to access reaction cuvettes 26. Processing devices 34 are adapted to provide, among other processing steps, for mixing together of the sample liquid and the reagent liquid contained in cuvettes 24, for washing the sample liquid and the reagent liquid contained in cuvettes 24, and for magnetic separation of tagged magnetic particles from free tags or reagent liquid contained in cuvettes 24.

Various assay analyzing stations 66 may be located proximate outer reaction carousel 12 and are adapted to measure light absorbence in or emission from cuvettes 24 at various wavelengths, from which the presence of analyte in the sample liquid may be determined using well-known analytical techniques. Stations 66 typically comprise conventional photometric, fluorometric or luminescent measuring devices adapted to perform an interrogating measurement at any convenient time interval during which reaction carousel 12 is stationary.

Drive means are provided for independently rotating outer reaction carousel 12 about an axis, the drive means typically comprising gear teeth disposed on the carousel 12 and interlacing with pinion gears mounted on the shaft of a motor. The drive means may be of conventional design and are not illustrated.

Figure 5:
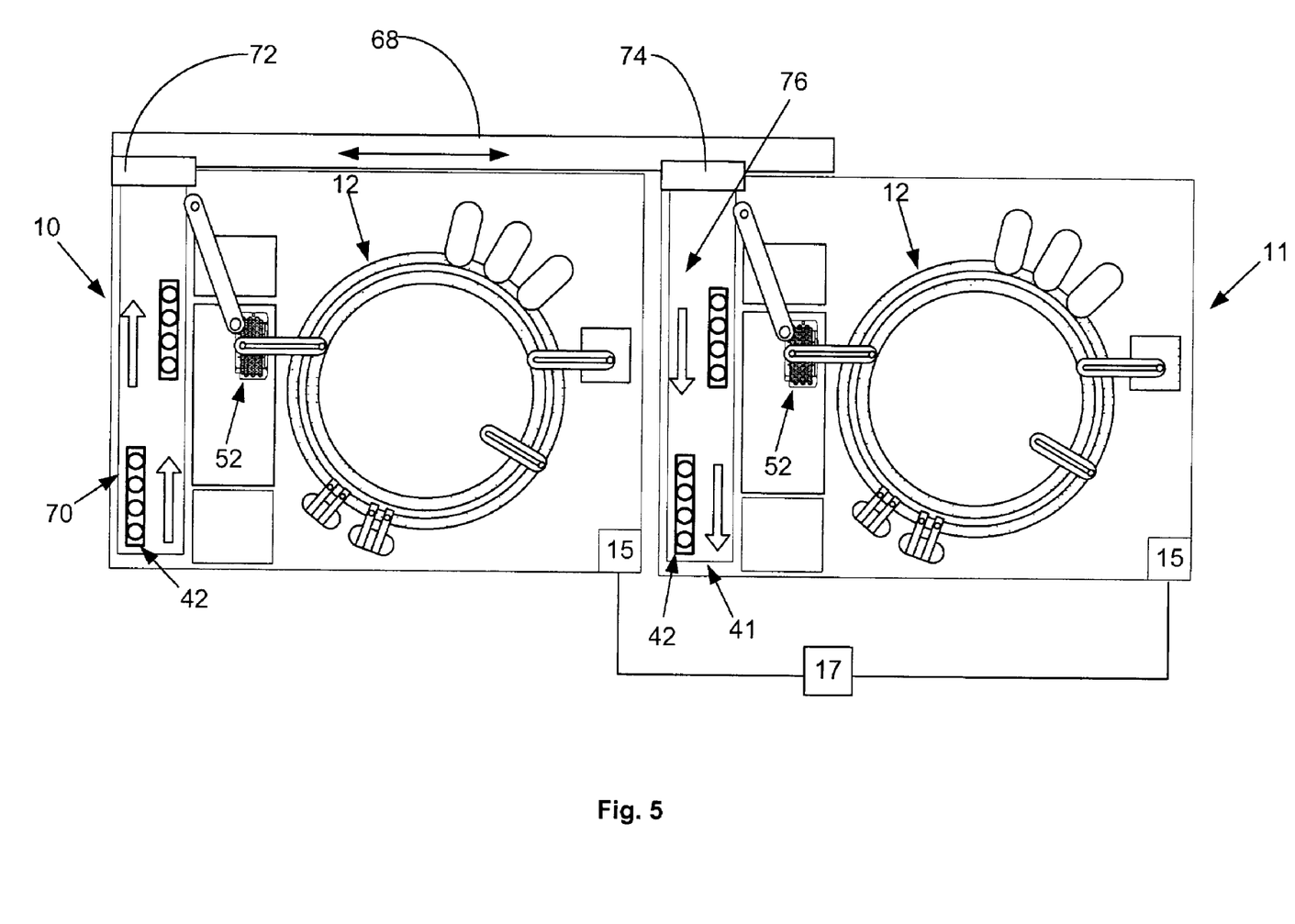
FIG. 5 is schematic plan view of a pair of automated clinical analyzers like those of FIG. 1, operated as taught by the present invention; and, FIG. 6 is a charted illustration of the ranking of frequency of different assays typically requested in a clinical laboratory.

A principal object of the invention is to provide a method for operating a pair of automatic clinical analyzers 10 linked together by a bi-directional sample rack shuttle 68 as shown in FIG. 5 in a manner that optimizes throughput irregardless of the mix of different assays required to be performed for different samples to be tested. In this instance, the individual computers 15 of analyzers 10 may be cooperatively controlled by a stand-alone computer 17 so programmed using well known techniques, or a single one of the computers 15 may alternately be programmed so as to control both analyzers 10 and 11.

Analyzers 10 are essentially identical to one another except that the menu of assays capable of being performed thereon is selectively different as explained later. For convenience in describing operation of the pair of automatic clinical analyzers 10, the rightmost analyzer is identified an analyzer 11. In this arrangement, the bi-directional incoming and outgoing sample tube transport system 36 of analyzer 10 is converted into a one-way incoming sample tube transport system 70 adapted to receive all sample tube racks 42 having sample tubes 40 to be analyzer by either analyzer 10 or 11. Any sample tube rack 42 may then be transferred from incoming sample tube transport system 70 by a conventional transfer mechanism 72 operable between analyzer 10 and bi-directional sample rack shuttle 68 and shuttled from shuttle 68 via a similar transfer mechanism 74 onto analyzer 11 as directed by computer 17. In a similar manner, the incoming sample tube transport system 36 of analyzer 11 may be converted into a one-way outgoing transport system 76 adapted to dispose of all sample tube racks 42 having sample tubes 40 with samples finally analyzed by either analyzer 10 or 11. Operation and features of a transport mechanism like sample rack shuttle 68 are well known in the art, for example as discussed in U.S. Pat. Nos. 6,117,392 and 6,117,683 and 6,141,602, and are thus not provided here. Generally, conveyor belts, hooks, magnetic devices, or the like may be employed in the design of transport system 70, transfer mechanism 72 and transfer mechanism 74.

An important feature of the method is a unique partitioning of the assays to be performed into groups defined by the frequency of testing using the individual assays and assigning different groups to different analyzers. Hereinafter the term "menu assays" is intended to mean the full number of assays analyzers 10 and 11 are designed for and capable of being performed including necessary reagents or other specialty items being loaded onto the analyzer. For the purpose of illustration only, consider a first embodiment of the present invention in which a larger percentage, for example 75–90%, of the most frequently menu assays requested to be performed are assigned into a first subgroup, identified as Group A. Importantly, the total number of different assays in Group A comprise a smaller number of the total number of different menu assays. In this instance, analyzer 10, hereinafter referred to as the "upstream analyzer 10", may be selectively adapted to perform all the assays within Group A, and analyzer 11, hereinafter referred to as the "downstream analyzer 11", may be similarly adapted to perform the same totality of assays within Group A.

Figure 6:
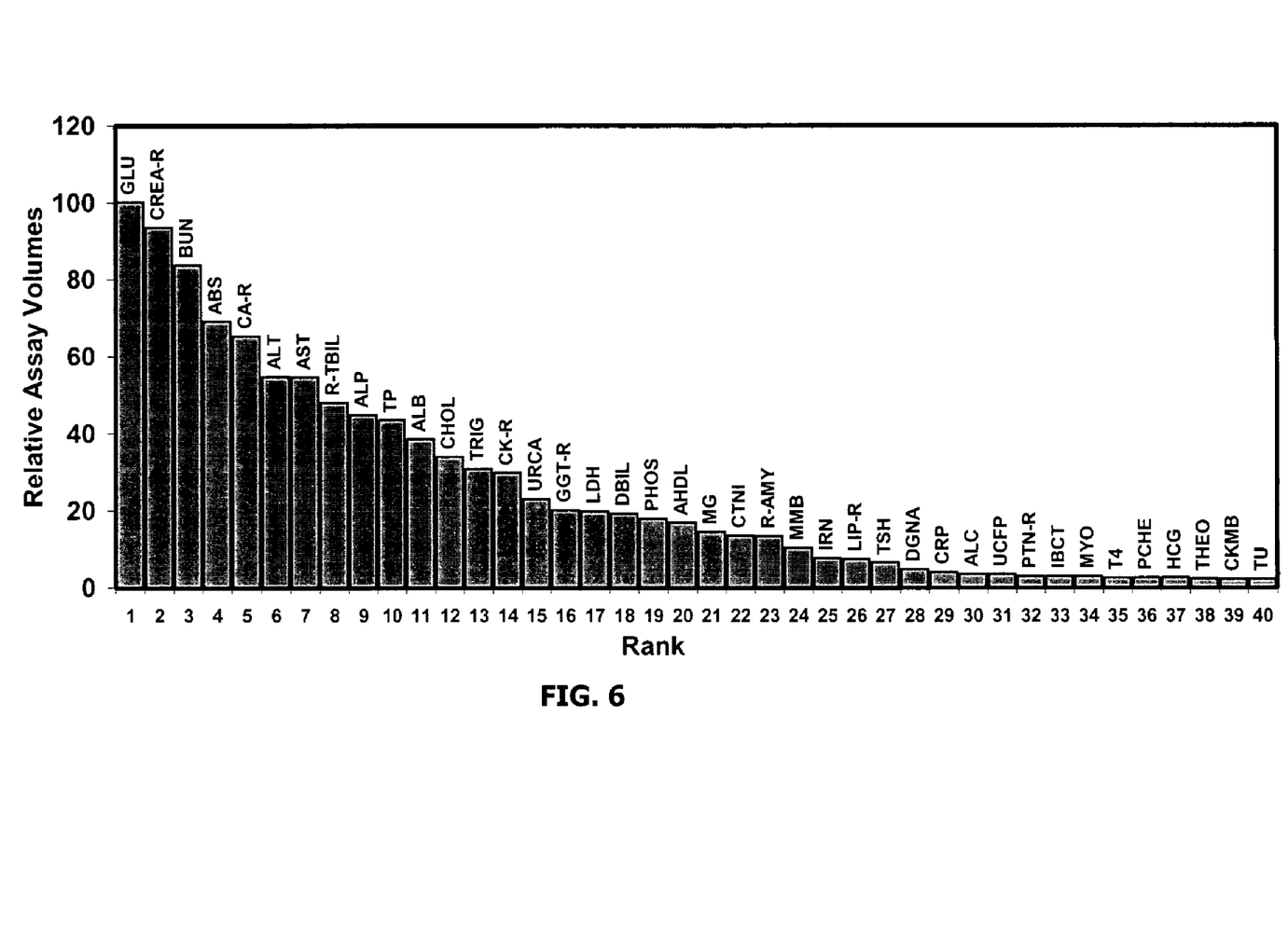

The remaining assays within the full list of menu assays are divided into two other groups, a second subgroup, Group B, and a third subgroup, Group C, so that the totality of assays assigned into Groups A, B, and C comprise the full list of menu assays. The different assays in Groups B and C comprise a smaller percentage, for example 25–10%, of the most frequently menu assays requested to be performed. Importantly, the total number of different assays in Groups B and C comprise a larger number of the total number of different menu assays, even though their frequency of being requested is a smaller number of the total number of requested menu assays. Preferably, the totality of menu assays assigned into Groups B and C are divided so that each separate Group B and C comprises approximately equal percentages of those menu assays not assigned into Group A, on the basis of the frequency being requested within the full list of menu assays. FIG. 6 is a charted illustration of the ranking of frequency at which different assays, identified using conventional clinical abbreviations for their identification, might typically be requested to be performed in a clinical laboratory and thereby illustrates this operational feature of the present invention. In FIG. 6, the Group A assays would generally be found in the leftmost half of the graph, i.e., assays ranked from 1 to about 20 in terms of frequency of being requested and the Group B and C assays would generally be found in the rightmost half of the graph, i.e., assays ranked from about 21 to about 40. It is not critical in performing the present invention how the Group B and C assays are selected from among those in the rightmost half of the graph, except that as mentioned earlier, each Group B and C comprises approximately equal percentages of those menu assays not assigned into Group A.

A key feature of the present invention is that the upstream analyzer 10 would be equipped with necessary reagents or other specialty items as required to perform all of those assays of Group B, in addition to being equipped with necessary reagents or other specialty items as required to perform all of those assays the assays within Group A, but would not be equipped with necessary reagents or other specialty items as required to perform any of those assays of Group C. Similarly, the downstream analyzer 11 would be analyzer 10 would be equipped with necessary reagents or other specialty items as required to perform all of those assays of Group C, in addition to being equipped with necessary reagents or other specialty items as required to perform all of those assays the assays within Group A, but would not be equipped with necessary reagents or other specialty items as required to perform any of those assays of Group B. This limitation is not intended to imply that analyzers 10 and 11 are not physically capable to perform any and all of the full menu assays, but only that analyzers 10 and 11 have reagents stored on-board so that only Group A and Group B assays may be performed by analyzer 10 and Group A and Group C assays may be performed by analyzer 11.

For the purpose of illustrating this first embodiment, Table 1 is provided below with an exemplary listing of typical clinical and immunoassays for the Groups A, B and C assays. This listing is not intended to be definitive nor limiting in any manner. In practice, however, the assays in Group A do comprise approximately 80–85% of the totality of assay tests requested to be performed by analyzers 10 and 11 and the assays in Group B and Group B do comprise approximately 10–12% each of the remainder of said totality of tests. It should be noted that the frequency of assays requested by a number of different physicians to be performed varies both regionally and demographically, so that FIG. 6 and Table 1, while generally illustrative of actual clinical experience, are intended to be representative only.

TABLE 1

| ASSAY GROUP A | ASSAY GROUP B | ASSAY GROUP C |
| --- | --- | --- |
| Glucose | Magnesium | Troponin I |
| Creatinine | Amylase | Mass CKMB |
| Urea Nitrogen | Iron | Lipase |
| Calcium | Phenytoin | Thyroid Stimulating Hormone |
| Alanine Aminotransferase | Myoglobin | C-Reactive Protein |
| Aspartate Aminotransferase | Pseudocholinesterase | Urine CFP |
| Total Bilirubin | Theophylline | Myoglobin |
| Alkaline Phosphatase | Thyronine Uptake | Thyroxine |
| Total Protein | Ammonia | Human Chorionic Gonadotropin |
| Albumin | Total Iron binding Capacity | Theophylline |
| Cholesterol | Free T4 | Ferritin |
| Triglyceride | Hemoglobin A1C | Vancomycin |
| Creatine Kinase | Phenobarbital | Carbamazepine |
| Uric Acid | Lactic Acid | Phenobarbital |
| □-Glutamyl Transferase | Prostate Specific Antigen | Valproic Acid |
| Lactic Dehydrogenase | Ammonia | Prealbumin |
| Direct Bilirubin | Transferrin | Cocaine Metabolite |
| Phosphorus | Opiates | Gentamicin |
| HDL Cholesterol | Benzodiazepines | Salicylate |

As a matter of further explanation, a very simplified operation of analyzers 10 and 11 with one each of a Type A, B and C assays requested to be performed in a selected time period will be described. In this example, 85 of the most frequently requested assays are to be performed by analyzers 10 and 11, for example, 26 Glucose, 24 Creatinine, 20 Urea Nitrogen, and 14 Calcium assays, and these are characterized as Type A assays. Further, 6 of the less frequently requested assays are to be performed by analyzers 10 and 11, for example, 2 Magnesium, 2 Amylase, 1 Iron Nitrogen, and 1 Phenytoin assays, and these are characterized as Type B assays. Finally, 6 other of the less frequently requested assays are to be performed by analyzers 10 and 11, for example, 2 Troponin I, 2 Mass CKMB, 1 Lipase, and 1 Thyroid Stimulating Hormone assays, and these are characterized as Type C assays.

As the sample tube containers 40 containing patient sample for these requested assays are identified by bar-code scanning and coupled with data contained in computer 17 for operating the dual system of analyzers 10 and 11, sample tube racks 42 having the corresponding patient sample fluids for 13 Glucose, 12 Creatinine, 10 Urea Nitrogen, and 7 Calcium assays, which have been characterized as Type A assays are moved into aliquot strip transport system 50 of analyzer 10 where arm 44 aspirates liquid sample from sample tubes 40 and dispenses a sample aliquot into one or more of a plurality of aliquot wells 52W in aliquot vessels 52; sample aspiration and dispense arm 54 is controlled by computer 15 to aspirate a controlled amount of sample from wells 52W via a nozzle 54N and to dispense an appropriate amount of aspirated sample into one or more cuvettes 24 for Type A assay testing on analyzer 10. In addition, in accord with the present invention, sample tube racks 42 having the corresponding patient sample fluids for 2 Magnesium, 2 Amylase, 1 Iron Nitrogen, and 1 Phenytoin assays, which have been characterized as Type B assays are moved into aliquot strip transport system 50 of analyzer 10 liquid sample from sample tubes 40 is removed and placed into one or more cuvettes 24 for Type B assay testing on analyzer 10.

Similarly, sample tube racks 42 having the corresponding patient sample fluids for 13 other Glucose, 12 other Creatinine, 10 other Urea Nitrogen, and 7 other Calcium assays, which comprise the remaining Type A assays are moved by incoming sample tube transport system 70 of analyzer 10 to transfer mechanism 72 between analyzer 10 and bi-directional sample rack shuttle 68 and shuttled from shuttle 68 via a similar transfer mechanism 74 onto analyzer 11 into outgoing transport system 76 of analyzer 11 as directed by computer 17. Transport system 76 moves the appropriate sample tube racks 42 into aliquot strip transport system 50 of analyzer 11 where arm 44 aspirates liquid sample from sample tubes 40 and dispenses a sample aliquot into one or more of a plurality of aliquot wells 52W in aliquot vessels 52; sample aspiration and dispense arm 54 is controlled by computer 17 to aspirate a controlled amount of sample from wells 52W via a nozzle 54N and to dispense an appropriate amount of aspirated sample into one or more cuvettes 24 for Type A assay testing on analyzer 11. In addition, in accord with the present invention, sample tube racks 42 having the corresponding patient sample fluids for 2 Troponin I, 2 Mass CKMB, 1 Lipase, and 1 Thyroid Stimulating Hormone assays, which have been characterized as Type C assays are moved into aliquot strip transport system 50 of analyzer 11, liquid sample from sample tubes 40 is removed and placed into one or more cuvettes 24 for Type C assay testing on analyzer 11.

During this procedure, it is apparent that occasions will arise when a single sample tube rack 42 contains one or more tubes 40 having patient sample for which both Type B and C assays have been requested. In such an instance, the sample tubes 40 having requirements for Type B assays may be first moved into aliquot strip transport system 50 of analyzer 10 where a sample aliquot is placed into aliquot wells 52W in aliquot vessels 52 prior to being placed in one or more cuvettes 24 for Type B assay testing on analyzer 11. The sample rack 42 may then be returned onto incoming sample tube transport system 70 of analyzer 10 and moved via transfer mechanism 72 between analyzer 10 and bi-directional sample rack shuttle 68 and shuttled from shuttle 68 via transfer mechanism 74 onto analyzer 11 where sample tubes having requirements for Type C assays may be moved into aliquot strip transport system 50 of analyzer 11 and a sample aliquot placed into aliquot wells 52W prior to being placed in one or more cuvettes 24 for Type C assay testing on analyzer 11.

In an alternate embodiment of the invention, only analyzer 10 would be equipped with necessary reagents or other specialty items as required to perform all of the Type A assays requested and would not be equipped to perform any of the Type B and Type C assays. In this alternate embodiment, analyzer 11 would be equipped with necessary reagents or other specialty items as required to perform all of the Type A assays requested and would also be equipped to perform all of the Type B and Type C assays requested. Such an embodiment has the back-up reliability features of the first embodiment, however throughput of the most frequently requested assays of the first subgroup is increased.

The details of performing a myriad of such assays as Type A, B and C within a dual analyzer system is a task regularly encountered within the art and need not be described herein. It is sufficient that the teachings of the present invention, that partitioning assays by frequency of request and providing appropriate reagents storage and access probes dedicated to the different types, need only be presented to such artisans so that an previously unachievable increase in analyzer throughput be achieved. It is to be understood that the embodiments of the invention disclosed herein are illustrative of the principles of the invention and that other modifications may be employed which are still within the scope of the invention. For these reasons, the present invention is not limited to those embodiments precisely shown and described in the specification but only by the following claims.

We claim:

1. A method of operating an analytical analyzer system comprising first and second analyzers each analyzer adapted to perform numerous different assays on a plurality of different samples, the method comprising:
   partitioning the assays to be performed into first, second and third groups wherein the first group comprises most frequently requested assays, the second group comprises one set of less-frequently requested assays and third group comprises a second set of less-frequently requested assays, the first and second sets consisting of different assays;
   operating the first analyzer to conduct assays only for a first combination of two of the three separate groups; and,
   operating the second analyzer to conduct assays only for a second combination of the three separate groups, wherein the first and second combinations are different and have only the first group in common.

2. The method of claim 1 wherein the totality of assays assigned into the second and third groups are divided so that each of the second and third groups comprises approximately equal percentages of those assays not assigned to the first group.

3. The method of claim 1 wherein the analytical analyzer system is operated so that an incoming sample to be assayed with an assay is assayed on the second analyzer only when the first analyzer is not adapted to perform said assay.

4. The method of claim 1 wherein the analytical analyzer system is operated so that an incoming sample to be assayed with an assay is assayed on the second analyzer only when the first analyzer is already scheduled to perform a number of said assays.

* * * * *

UNITED STATES PATENT AND TRADEMARK OFFICE
CERTIFICATE OF CORRECTION

PATENT NO. : 7,101,715 B2 Page 1 of 1
APPLICATION NO. : 10/245245
DATED : September 5, 2006
INVENTOR(S) : Devlin, Sr. et al.

It is certified that error appears in the above-identified patent and that said Letters Patent is hereby corrected as shown below:

1) In the Abstract, line 10 please delete the word "be".

2) In the Abstract, line 11 please delete the word "second" and insert -- first --.

Signed and Sealed this

Tenth Day of April, 2007

JON W. DUDAS
*Director of the United States Patent and Trademark Office*